(12) United States Patent
Onishi et al.

(10) Patent No.: US 7,918,234 B2
(45) Date of Patent: Apr. 5, 2011

(54) WASHER DISINFECTOR EQUIPPED WITH BATH TO WHICH TRAY WITH ENDOSCOPE MOUNTED THEREON IS DETACHABLY LOADED

(75) Inventors: Hideto Onishi, Tokyo (JP); Eiri Suzuki, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 528 days.

(21) Appl. No.: 11/956,866

(22) Filed: Dec. 14, 2007

(65) Prior Publication Data
US 2008/0142049 A1  Jun. 19, 2008

(30) Foreign Application Priority Data
Dec. 14, 2006  (JP) ................................. 2006-337362

(51) Int. Cl.
- B08B 11/02 (2006.01)
- B08B 3/04 (2006.01)
- B08B 9/032 (2006.01)
- B08B 9/053 (2006.01)

(52) U.S. Cl. .................. 134/43; 134/166 C; 134/167 R; 134/198

(58) Field of Classification Search .................. 134/43, 134/56 R, 58 R, 166 R, 170, 169 R, 198; 600/101
See application file for complete search history.

(56) References Cited

U.S. PATENT DOCUMENTS
| | | |
|---|---|---|
| 2005/0000553 A1 | 1/2005 | Noguchi et al. |
| 2005/0209507 A1 | 9/2005 | Suzuki et al. |
| 2007/0107152 A1* | 5/2007 | Noguchi et al. ......... 15/104.095 |

FOREIGN PATENT DOCUMENTS
| | | |
|---|---|---|
| EP | 1 785 148 A2 | 5/2007 |
| EP | 1 785 150 A1 | 5/2007 |
| JP | 2006-095084 | 4/2006 |

* cited by examiner

Primary Examiner — Michael Kornakov
Assistant Examiner — Natasha Campbell
(74) Attorney, Agent, or Firm — Scully, Scott, Murphy & Presser, PC.

(57) ABSTRACT

An endoscope washer disinfector washes and disinfects an endoscope with a mouth ring communicating with an endoscope duct. The washer disinfector comprises a washing disinfecting bath; a nozzle arranged with the bath, loaded into the mouth ring, and formed to supply fluid to the duct via the mouth ring; a tray on which the endoscope is mounted. In this washer disinfector, a bilateral positioning member positions the endoscope and the tray so that the mouth ring of the endoscope mounted on the tray is located at a given position on the tray; and a trilateral positioning member positions the washing disinfecting bath, the tray, and the endoscope so that, when the tray is loaded into the washing disinfecting bath, the mouth ring of the endoscope positioned at the given position on the tray by the bilateral positioning member is positioned at a position that is across is from the nozzle.

4 Claims, 11 Drawing Sheets

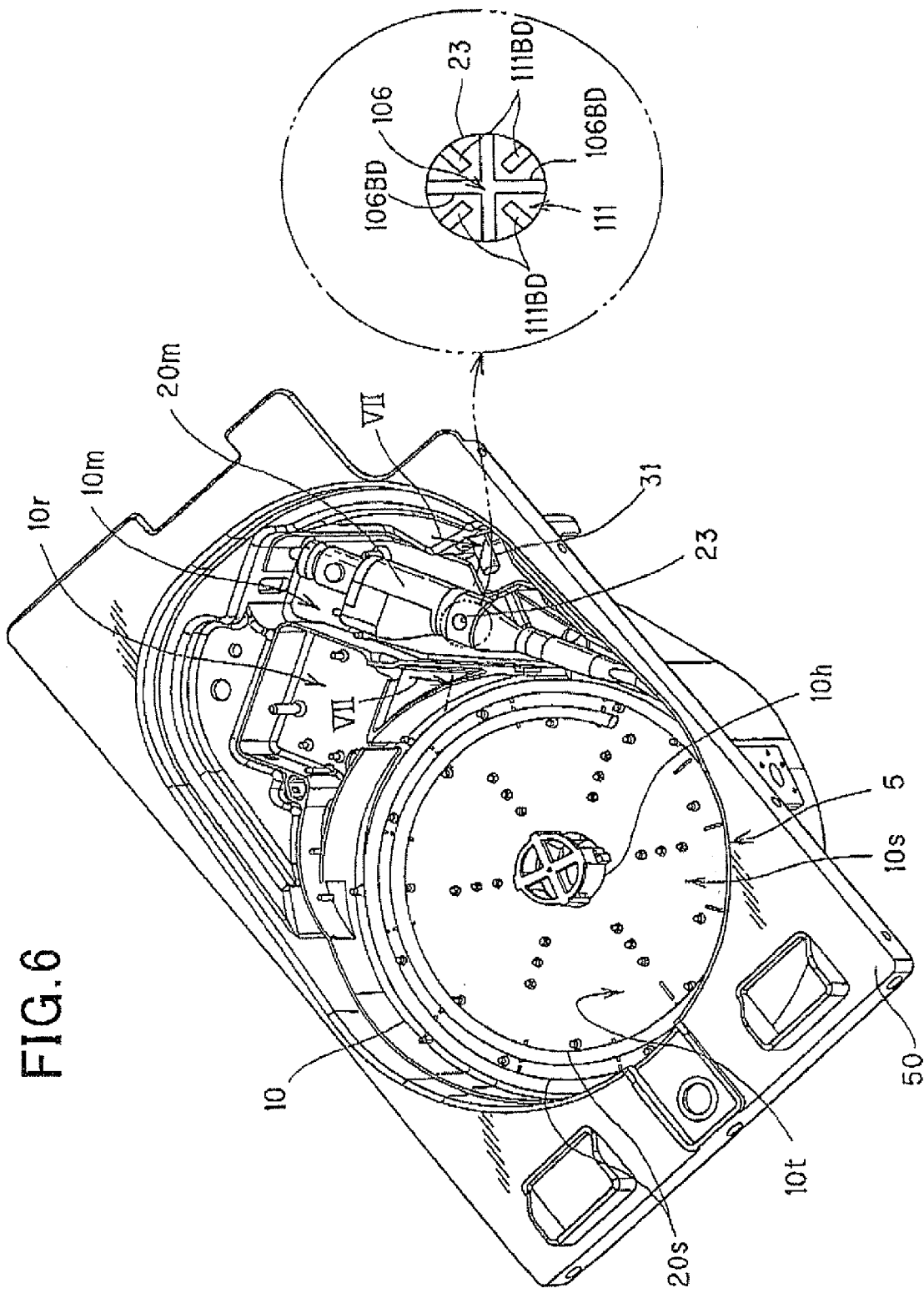

WASHER DISINFECTOR EQUIPPED WITH BATH TO WHICH TRAY WITH ENDOSCOPE MOUNTED THEREON IS DETACHABLY LOADED

CROSS REFERENCE TO RELATED APPLICATION

The present application relates to and incorporates by reference Japanese Patent application No. 2006-337362 filed on Dec. 14, 2006.

BACKGROUND OF THE INVENTION

1. The Field of the Invention

The present invention relates to a washer disinfector that washes and disinfects endoscopes for medical use (hereinafter referred to as an "endoscope washer disinfector") and, in particular, to an endoscope washer disinfector equipped with a washing disinfecting bath and automatically washes and disinfects an endoscope accommodated within the washing disinfecting bath.

2. Related Art

Medical endoscopes have now grown into indispensable modalities for inspection and treatment of patients' body cavities. Once such an endoscope is used, the outer surface of the insertion tube inserted into a body cavity as well as the insides of various ducts, such as the air-supply water-supply duct, suction duct, forward water-supply duct, and/or therapeutic duct, of the endoscope are polluted with waste materials. Hence it is necessary that the outer surface of a used endoscope and the insides of each duct thereof are always washed and disinfected.

In some cases, the washing and disinfection is performed by hand, but it is usual to use an endoscope washer disinfector, i.e., an apparatus for washing and disinfecting endoscopes. For using such an endoscope washer disinfector, a used endoscope is accommodated into a washing disinfecting bath, which is within the main body of this endoscope washer disinfector, and positionally fixed therein. For washing inside the ducts of the endoscope, the mouth rings of the ducts, which are open to the outside, are connected to various nozzles within the washer disinfector via tubes. The nozzles, which are for supplying various kinds of fluid and gas necessary for washing and disinfection, are arranged as part of a supply unit attached to the washing disinfecting bath. The supply unit is arranged to receive the various kinds of fluid and gas from containers.

The washing disinfecting bath is then closed by a lid member attached thereto, before a start switch is set "on" for starting the processes of washing and disinfection. In response to this, the washer disinfector performs a water leakage check to confirm whether the endoscope has a water leakage. If there is no water leakage, processes including a washing step, a rinsing step, a disinfecting step, and a drying step are performed in sequence.

In this way, the endoscope washer disinfector is known which has the capability of washing and disinfecting the insides of the ducts as well as the outer surface of the endoscope. However, for washing and disinfecting the insides of the ducts, it is necessary to connect by hand the fluid supply nozzle to each mouth ring of the ducts using tubes. This connection work of the tubes is inconvenient for operators.

There is also known an endoscope washer disinfector which is able to eliminate the user's work in connecting the tubes. This washer disinfector is equipped with a fluid supply unit with fluid supply nozzles to be connected automatically to the mouth rings of the ducts of an endoscope. In this unit, however, it is necessary to position, with high accuracy, the endoscope in the washing disinfecting bath. Without such high accuracy, the automatic connection cannot be performed, because the relative positions between the supply nozzles and the mouth rings deviate from the correct ones. This results having to reset the endoscope in the washing disinfecting bath, thus decreasing the efficiency of the process.

To remove such inconveniences, there is also known an endoscope washer disinfector disclosed by Japanese Patent Application Publication (Laid-open) No. 2006-95084. In this washer disinfector, circular grooves formed on the insertion tube and manipulating device of an endoscope are engaged with support members standing up from the washing disinfecting bath. This allows the respective mouth rings to be positioned relative to the supply nozzles with precision. Hence the endoscope can be accommodated at the right position in the bath.

However, the endoscope washer disinfector according to the foregoing publication is also confronted with another difficulty. Once an endoscope is used for an examination and/or a treatment, it is normal that the endoscope is subjected to adhesion of contamination from body fluid, blood, and others. It is thus necessary to prevent the contamination from spreading to personnel and surroundings during the delivery of endoscopes to the washer disinfector. Thus, it is usual that a used endoscope is mounted on a dedicated tray and delivered to the washer disinfector.

When being delivered to the washer disinfector using the tray, the used endoscope is then accommodated into the washing disinfecting bath in one of two ways. One way is to accommodate the endoscope using the engagement mechanism described in Japanese Patent Application Publication (Laid-open) No, 2006-95084. The other way is to make use of the tray itself. That is, with the endoscope kept mounted on the tray, the tray is loaded into the washing disinfecting bath. This kind of endoscope washer disinfector is known as well.

Of course, even when a dedicated tray is used, it is absolutely necessary to accurately position the mouth rings of the endoscope ducts relative to the fluid supply nozzles. Specifically, a used endoscope should be set accurately in position on the tray, and the tray should be set accurately within the washing disinfecting bath.

It is therefore understood that accurately positioning an endoscope (i.e., its ducts) relative to the fluid supply nozzles needs a two-stage positioning procedure. One stage is positioning between the endoscope and the tray, while the other stage is positioning between the tray and the washing disinfecting bath. Each positioning should be accurate. If any one of the two-stage positioning procedures results in poor accuracy, it is difficult to accurately position the endoscope ducts relative to the fluid supply nozzles. Therefore, using the tray is inferior in positioning accuracy to the case where an endoscope is directly mounted in the bath.

SUMMARY OF THE INVENTION

The present invention has been made in consideration of the above difficulties, and an object of the present invention is to provide an endoscope washer disinfector which is able to give higher positioning accuracy between a mouth ring of the endoscope, which communicate with a duct formed therethrough, and a nozzle for supplying fluid necessary for washing and disinfection to the mouth ring, when a tray with the endoscope mounted thereon is loaded into the washing disinfecting bath of an endoscope washer disinfector.

In order to achieve the above object, as one aspect of the present invention, there is provided an endoscope washer disinfector for washing and disinfecting an endoscope equipped with a mouth ring communicating with a duct formed within through the endoscope. The endoscope washer disinfector comprises a washing disinfecting bath in which the endoscope is accommodated; a nozzle arranged within the washing disinfecting bath, loaded into the mouth ring of the endoscope, and in charge of supplying fluid to the duct via the mouth ring; and a tray on which the endoscope is mounted and which is detachably loaded into the washing disinfecting bath. The endoscope washer disinfector further comprises a bilateral positioning member and a trilateral positioning member. The bilateral positioning member positions the endoscope and the tray so that the mouth ring of the endoscope mounted on the tray is located at a given position on the tray. The trilateral positioning member positions the washing disinfecting bath, the tray, and the endoscope so that, when the tray is loaded into the washing disinfecting bath, the mouth ring of the endoscope positioned at the given position on the tray by the bilateral positioning member is positioned at a position that is across from the nozzle.

According to the present invention, when the tray, on which a used endoscope is mounted, is loaded into the washing disinfecting bath of the endoscope washer disinfector, the bilateral and trilateral positioning members work so that the mouth ring of the endoscope is highly accurately located at the position facing the nozzle.

BRIEF DESCRIPTION OF THE DRAWINGS

In the accompanying drawings:

FIG. 6 is a perspective view showing a tray and a washing disinfecting bath unit of the endoscope washer disinfector according to a second embodiment of the present invention;

DETAILED DESCRIPTION OF THE PREFERRED EMBODIMENTS

With reference to the accompanying drawings, preferred embodiments of the drawings will now be described.

First Embodiment

Referring to FIGS. 1-5A and 5B, an endoscope washer disinfector according to a first embodiment of the present invention will now be described. In the following, detailed descriptions will be given to major components of the features of the present invention, while descriptions to the other parts are either simplified or outlined.

Figure 1:
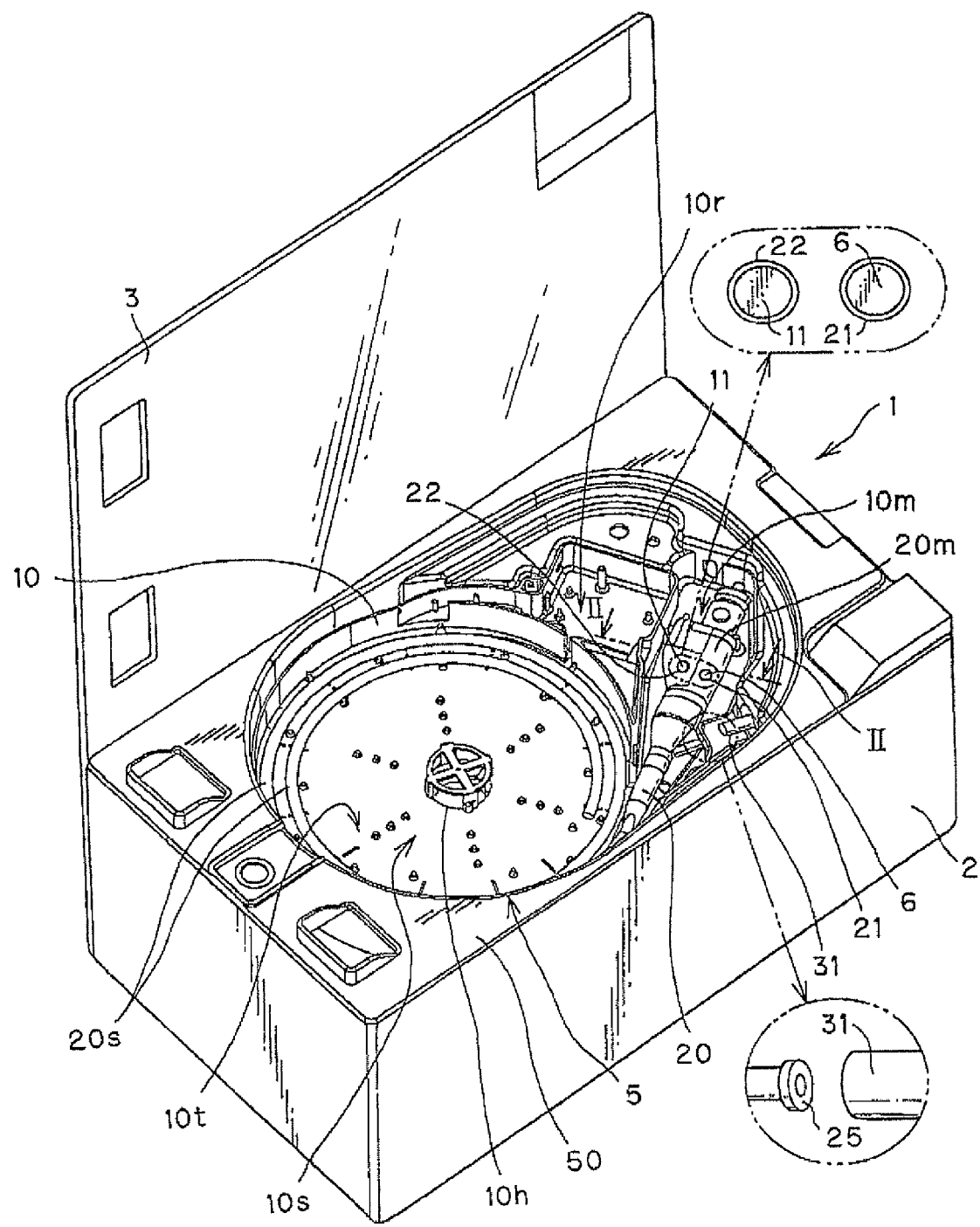
FIG. 1 is a perspective view showing an endoscope washer disinfector according to a first embodiment of the present invention, in which a tray with a used endoscope mounted is loaded into a washing disinfecting bath of the washer disinfector.

As shown in FIG. 1, there is provided an endoscope washer disinfector 1 for washing and disinfecting a used endoscope 20 and accessories thereof. The endoscope washer disinfector 1 is equipped, as its major components, with a main body 2 and a cover 3 which can open and close the top of the main body 2 by for example hinges fixed to an edge of the top.

Figure 4:
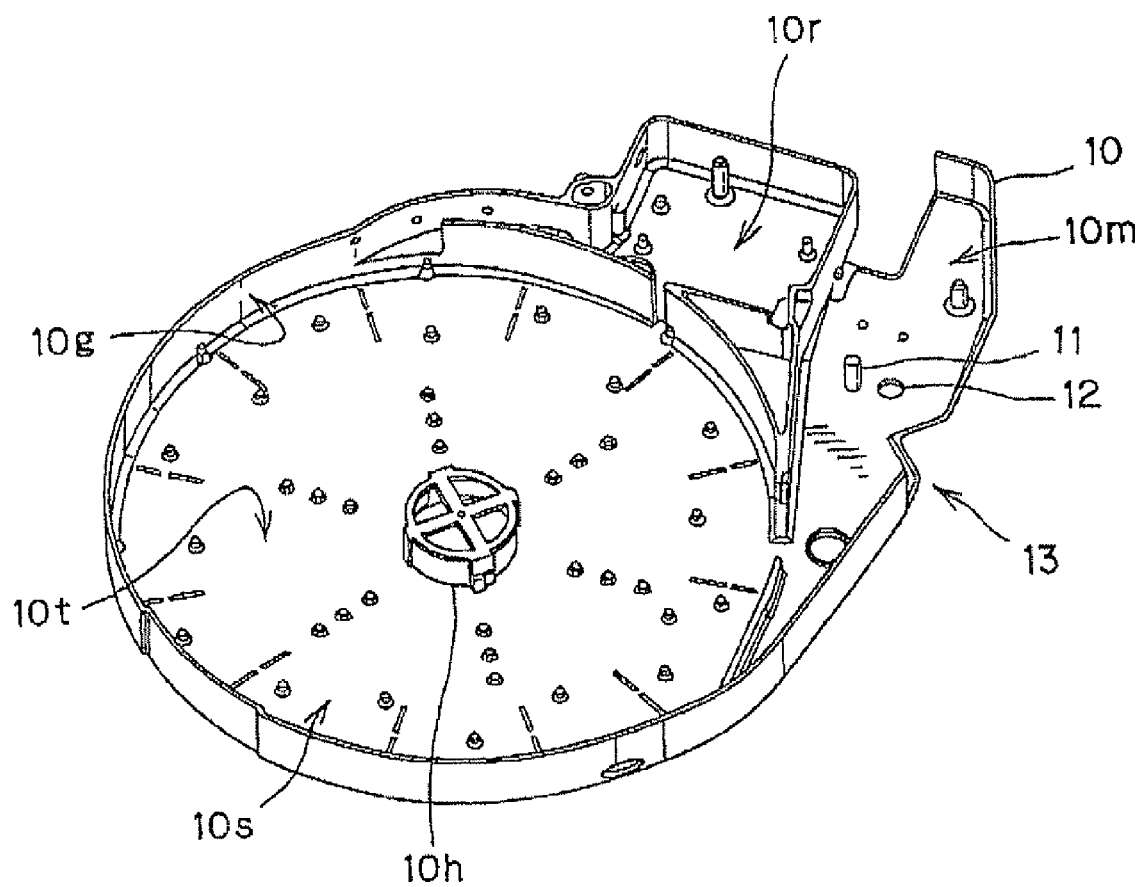
FIG. 4 is a perspective view showing the tray to be loaded into the washing disinfecting bath.
Figure 5A:
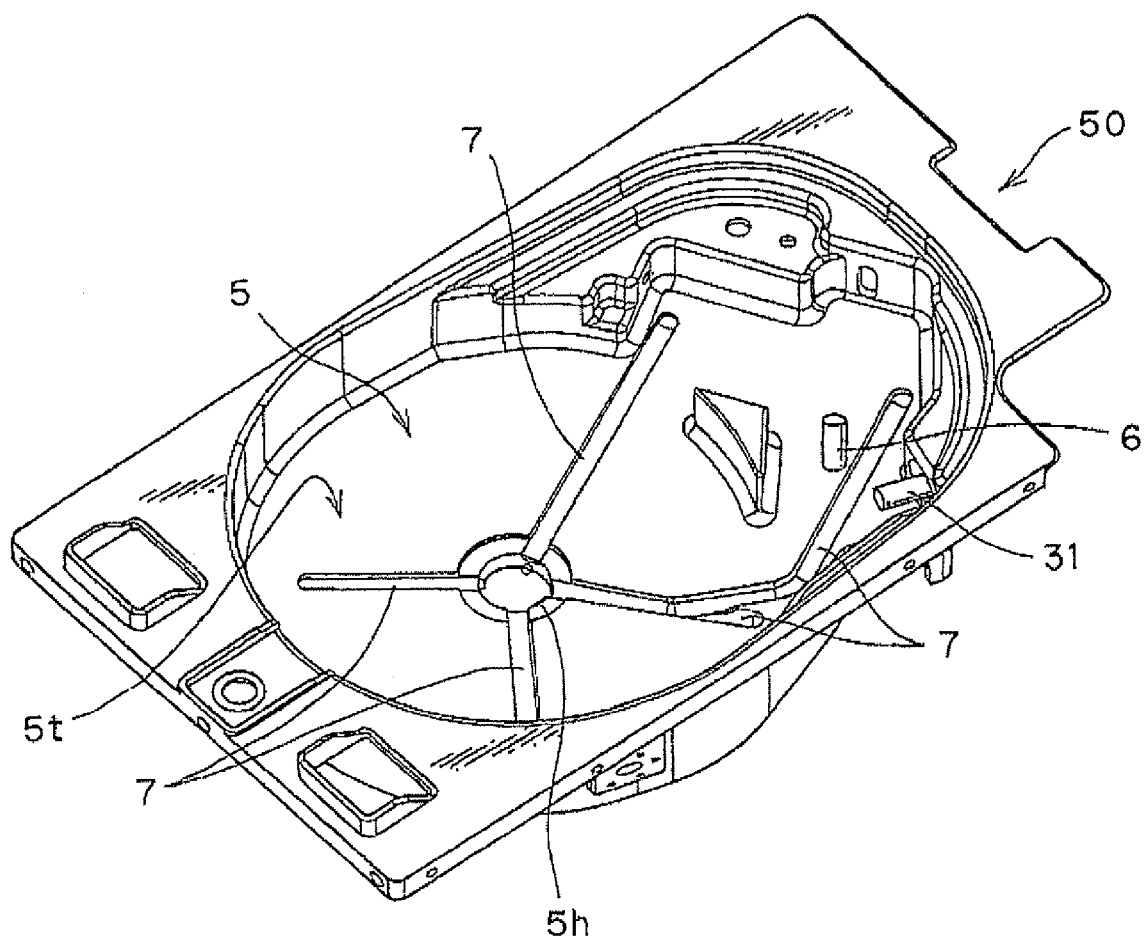
FIG. 5A is a perspective view showing the washing disinfecting bath.
Figure 5B:
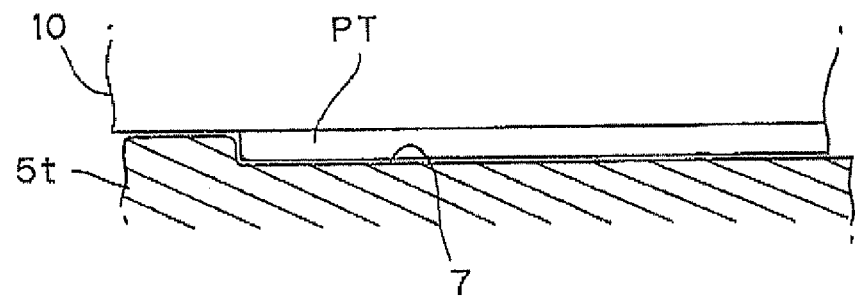
FIG. 5B is a partial sectional view that explains a structure to orient the direction of the endoscope.

At a top part of the main body 2, a washing disinfecting bath unit 50 is arranged to provide a washing disinfecting bath 5. This bath 5 has a given depth as illustrated in FIG. 5A and has an opening facing upward, through which an endoscope 20 is inserted end removed. A tray 10, on which an endoscope 20 is placed to be held thereon as shown in FIG. 4, is detachable to and from the washing disinfecting bath 5.

In the main body 2, as shown in FIG. 1, a not-shown fluid supply unit is placed to automatically supply various types of fluid, such as liquid (including washing liquid, disinfectant liquid, and rinsing water) and gas (including air), to each duct (called "channel" of an endoscope 20 accommodated within the washing disinfecting bath 5. The fluid supply unit comprises a nozzle 31 to supply such a fluid and is located outside the washing disinfecting bath 5 so that the nozzle 5 is directed toward the bath 5.

In the endoscope 20, there are formed various ducts (i.e., channels) which include an air-supply water-supply duct, a forward water-supply duct, and a therapeutic-instrument insertion duct serving a suction duct as well. In the present embodiment, of those various types of ducts, the nozzle 31 will now be explained as a nozzle member to automatically supply fluid into the therapeutic-instrument insertion duct. The nozzle 31 is structured to be automatically connected with a mouth ring (or mouth piece) 25 (refer to FIG. 3) of the therapeutic-instrument insertion duct, which is also known. In addition, the structure of the fluid supply unit is known. Those known structures will be omitted from the following explanations.

As shown in FIG. 5A, the washing disinfecting bath 5 has a bottom 5t, in which there is formed a drain outlet 5h to drain away, from the washing disinfecting bath 5, various types of fluid such as washing liquid, disinfectant liquid and rinsing water at a central part of the bottom of the bath. Further, on the bottom 5t, there are formed plural linear grooves 7 which serve as locating means for the tray 10. These grooves 7 extend substantially radially along the face of the bottom.

The plural grooves 7 guide the liquid in the washing disinfecting bath 5 to the drain outlet 5h. In addition, the plural grooves 7 function to decide the loading direction of the tray 10 relative to the washing disinfecting bath 5. That is, plural tubular convex parts PT are formed on the rear face of the tray 10 (refer to FIG. 5B). The convex parts PT can be fit into the grooves 7, when the tray 10 is loaded into the washing disinfecting bath 5, so that the tray 10 can be oriented automatically in the bath.

Figure 3:
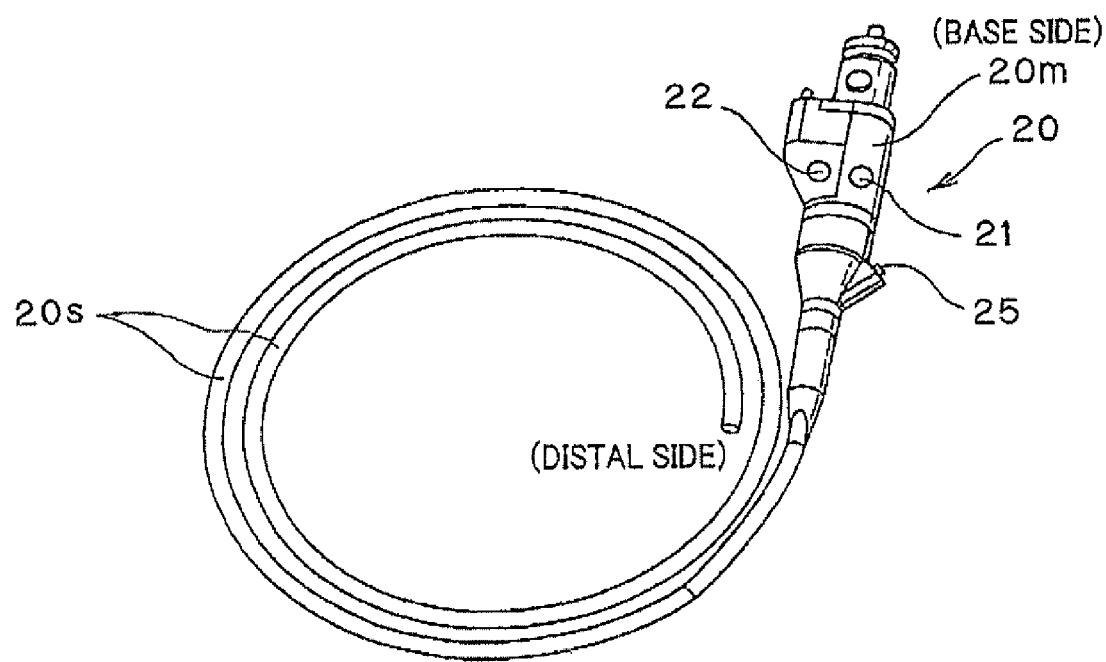
FIG. 3 is a perspective view showing the endoscope to be accommodated in the washing disinfecting bath.

To be specific, the directions of the plural grooves 7 are designed such that a fluid-supply-nozzle insertion opening 13 (later described) (hereinafter simply referred to as an "insertion opening") of the tray 10 is located at a position where a supply nozzle 31 exists. Namely, the endoscope 20 has a manipulating device 20m and a mouth ring 25 located and formed on the manipulating device 20 and connected to the therapeutic-instrument insertion duct passing through the device 20m, as shown in FIG. 3. Hence the plural grooves 7 decide the loading direction of the tray 10 in a manner that the manipulating device 20m of the endoscope 20 accommodated in the tray 10 approaches the supply nozzle 31 and the mouth ring 25 thereof is located at a position, where the supply nozzle 31 can be connected automatically with the mouth ring 25.

At a position in the bottom 5t of the washer disinfector 5, a first positioning pin 6, which is thin and cylindrical, stands up. The pin position is adjacent to one of the grooves 7, which approaches the supply nozzle 31.

When the tray 10 which accommodates the endoscope 20 is loaded into the washing disinfecting bath 5, the first positioning pin 6 is fit into a first through-hole 21 (later described) formed at the endoscope 20 in a manner that all the circumferential surface of the first positioning pin 6 comes closely in contact with the first through-hole 21. This fitting operation allows the endoscope 20 to be located to the washing disinfecting bath 5. Furthermore, the first positioning pin 6 is made to penetrate through a first positioning-pin insertion hole 12 (refer to FIG. 4) formed in the tray 10, which will also be described later. This operation allows the tray 10 to be located to the washing disinfecting bath 5.

Concretely, the first positioning pin 6 has the capability to position both the tray 10 and the endoscope 20. In other words, by the first positioning pin 6, the endoscope 20 is arranged such that the manipulating device 20m of the endoscope 20 is made to approach the supply nozzle to have the mouth ring 25 thereof located at the automatic connection position facing the supply nozzle 31.

As shown in FIG. 4, the tray 10 is detachable from the washing disinfecting bath 5 and the endoscope 20 can be accommodated and removed into and from the tray 10. The tray 10 has an outer contour of size almost the same as that of the inner contour of the washing disinfecting bath 5, when being viewed vertically to the bath. The tray 10 is formed into a top-face-open case that comprises a side wall (plane) 10g standing up at from the surrounding edge of the base 10t.

On one side of the side wall 10g which faces the supply nozzle 31, an insertion opening 13 is located which allows the supply nozzle 31 to be inserted therethrough and which faces the mouth ring 25 of the endoscope 20 accommodated in the tray 10.

Furthermore, the bottom lot of the tray 10 has a rear side, which faces the washing disinfecting bath 5 when the tray 10 is loaded into the bath 5. On the rear side, the foregoing plural tubular convex parts PT (refer to FIG. 5B) are formed to be fit into the grooves of the bath 5. The tubular convex parts PT are not limited in their shape to the one described. An alternative example is that each convex part is composed of a plurality of locally protruded parts which form a line.

The endoscope 20 has, as its essential components, a thin and long flexible insertion tube 20s and a manipulating device 20m (refer to FIG. 3) integral with the insertion tube. The endoscope 20 is accommodated in the tray 10 in its rounded and wound attitude of the insertion tube 20s. The tray 10 provides a circular insertion-tube accommodation space 10s, in which the insertion tube 20s of the endoscope 20 can be accommodated, and a manipulating-device accommodation space 10m, in which the manipulating device 20m is accommodated (refer to FIG. 3). The tray 10 further provides a remote-control accommodation space 10r, in which a remote control can be accommodated. This remote control is used for manipulating the insertion tube 20s equipped with a bendable portion bendable using electronic power.

In a central part of the insertion-tube accommodation space 10s, there is formed a drain port 10h to drain away fluid, such as washing liquid, disinfectant liquid, rising water, and alcohol, to the outside thereof.

As described, in the manipulating-device accommodation space 10m, the insertion opening 13 is formed at the side wall 10g. In addition, on the bottom of that accommodation space 10m, there is the first positioning-pin insertion hole 12 through which the first positioning pin 6 is inserted, when the tray 10 is loaded into the washing disinfecting bath 5.

The first positioning-pin insertion hole 12 is formed to have a contour which is tightly in contact with the whole periphery of the first positioning pin 6. This insertion hole 12 is located to positionally correspond to the position of the first positioning pin 6 when the tray 10 is loaded into the washing disinfecting bath 5.

In the manipulating-device accommodation space 10m, a cylindrical second positioning pin 11 is formed to stand up from the bottom 10t. The position of this second positioning pin 11 is close to the first positioning-pin insertion hole 12.

Figure 2:
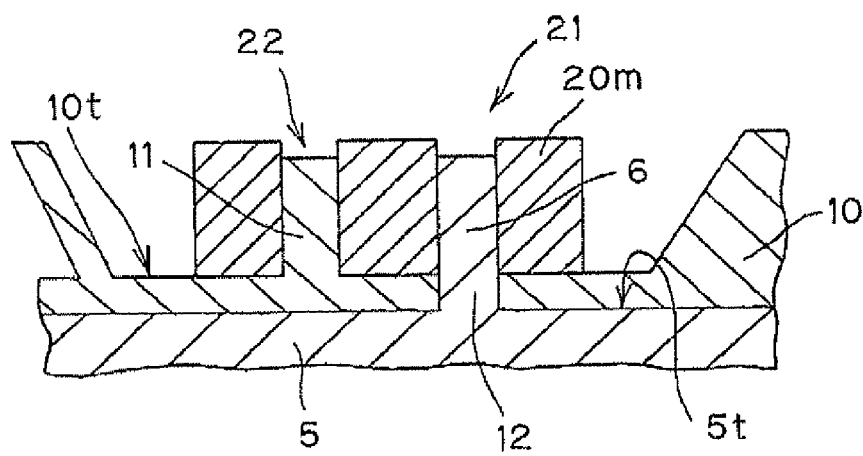
FIG. 2 is a partial sectional view taken along a II-II line shown in FIG. 1.

As shown in FIG. 2, in cases where the manipulating device 20m is accommodated in the manipulating-device accommodation space 10m, the second positioning pin 11 can be fitted into a later-described second through-hole 22 formed at the endoscope 20. Actually this insertion is carried out such that the entire periphery of this second positioning pin 11 closely contacts the second through-hole 22, thus enabling the endoscope 20 to be located relative to the tray 10.

Practically, the second positioning pin 11 is located so that the mouth ring 25 (refer to FIG. 3) of the endoscope 20 accommodated in the tray 10 is opposite to the insertion opening 13. According to this, when the tray 10 is loaded into the washing disinfecting bath 5, the second positioning pin 11 locates the endoscope 20 in the tray 10 such that the mouth ring 25 is fixed at the automatic connection position where the supply nozzle 31 directly faces the mouth ring 25.

As shown in FIG. 3, the manipulating device 20m of the endoscope 20 has the first through-hole 21, which is a positioning through-hole through which the first positioning pin 6 is tightly inserted, and the second through-hole 22, which is a positioning through-hole through which the second positioning pin 11 is tightly inserted.

The first through-hole 21 and the second through-hole 22 have diameters so that the though-holes 21 and 22 tightly accept the first and second positioning pins 6 and 11, respectively.

Each of the first and second through-holes 21 and 22 may not be limited to a through-hole like this embodiment, as this is not a definitive list. The through-holes may be replaced by bottomed holes.

As shown in FIG. 3, the mouth ring 25, which communicates with the therapeutic-instrument insertion duct, is mounted on the manipulating device 20m to be oblique by a given angle to an axis along the manipulating device 20m.

The operations and advantages of the endoscope washer disinfector according to the present embodiment will now be described.

For using the endoscope washer disinfector to wash and disinfect a used endoscope 20, the used endoscope 20 is first accommodated into the tray 10, before the tray 10 is loaded into the washing disinfecting bath 5. Concretely the insertion tube 20s is wound as illustrated in FIG. 3, and accommodated in the insertion-tube accommodating space 10s, as illustrated in FIG. 1, during which time the manipulating device 20m is placed into the manipulating-device accommodating space 10m.

When the manipulating device 20m is accommodated into the space 10m, the second positioning pin 11 standing up from the bottom 10t of the space 10m is tightly fit into the second through-hole 22 formed through the manipulating device 20m, as shown in FIGS. 1 and 2. As a result of this accommodation, the endoscope 20 in the tray is located to the tray 10 so that the mouth ring 25 is opposite to the insertion opening 13 of the tray 10.

As described above, the remote control is also accommodated into the remote-control accommodation space 10r of the tray 10.

Then the tray 10, in which the endoscope 20 is secured, is carried to the endoscope washer disinfector 1, and then loaded into the washing disinfecting bath 5. This loading action is performed as follows the tubular convex parts PT formed on the rear side of the bottom 10t (i.e., mounting plane) of the tray 10 are fitted into the grooves 7 formed on the bottom 5t of the washing disinfecting bath 5 so that the tray 10 is oriented firmly. Concurrently with this fitting action, as shown in FIGS. 1 and 2, the first positioning-pin insertion hole 12 of the tray 10 accepts the insertion of the first positioning pin 6 standing up from the bottom 5t. Further, concurrently with the fitting action, the first through-hole 21 of the manipulating device 20m accepts tight insertion of the first positioning pin 6, before completion of loading the tray 10 with the used endoscope 20 to the washing disinfecting bath 5.

As a result, a combination of the plural grooves 7 and the first positioning pin 6 allows the manipulating device 20m to be located close to the supply nozzle 31. By this close location, the mouth ring 25 of the endoscope 20 is present at the automatic connection position which is directly opposed to the supply nozzle 31, resulting in that the endoscope 20 is ready for washing and disinfection at the given position.

In this way, the endoscope 20, which is accommodated in the tray 10, is also accommodated and located with precision in the washing disinfecting bath 5. Then the top cover 3 is closed on the main body 2, and the endoscopic washer disinfector 1 is switched on. In response to this action, the supply nozzle 31 is moved the automatic connection position, where the nozzle 31 is automatically connected with the mouth ring 25 that has been located in front of the supply nozzle 31. This loading action is followed by supplying various types of fluid into the therapeutic-instrument insertion duct via the mouth ring 25 during each of the processing steps for washing and disinfection of the endoscope 20.

In the present embodiment, the plural grooves 7 are formed on the bottom 5t of the washing disinfecting bath 5 to orient the tray 10 to the given loading direction in the base 5. In addition, the manipulating device 20m of the endoscope 20 has the first through-hole 21 through which the first positioning pin 6 is fit for fixedly positioning both the tray 10 and the endoscope 20 relative to the bath 5.

Further, on the bottom lot of the manipulating-device accommodation space 10m of the tray 10, the first positioning-pin insertion hole 12 accepts the insertion of the first positioning pin 6 therethrough. At the same time, the second through-hole 22 of the manipulating device 20m accepts the insertion of the second positioning pin 11 so that the endoscope 20 is securely fixed relative to the tray 10.

Accordingly, when the endoscope 20 is accommodated into the tray 10, the second positioning pin 11 is inserted into the second through-hole 22. This inserting action makes it possible to position the endoscope 20 relative to the tray 10 such that its mouth ring 25 is in front of the insertion opening 13.

Moreover, the first positioning pin 6 is inserted into the first positioning-pin insertion hole 12 to cause the pin 6 to penetrate through the first through-hole 21. And the plural grooves 7 formed on the bottom 5t of the bath 5 are subjected to tight insertion of the tubular convex parts PT in a very simple manner. This insertion action makes it possible to position both the tray 10 and the endoscope 20 relative to the washing disinfecting bath 5. That is, the supply nozzle 31 is automatically placed at the automatic connection position, at which the supply nozzle 31 is movable toward the insertion opening 13. That is, the manipulating device 20m is located close to the supply nozzle 31 to permit the mouth ring 25 to be present at the automatic connection position.

Therefore, in the present endoscope washer disinfector 1, when the tray 10 is used to position the used endoscope 20 in the washing disinfecting bath 5, the user's operations to locate its mouth ring 25 to the supply nozzle 31 can be simplified, but still performed at high precision.

The foregoing loading operations and advantages resultant therefrom will not be limited to the therapeutic-instrument insertion duct of the endoscope 20, but are true of the other ducts. In the same manner as that described above, supply nozzles can be coupled to mouth rings mounted to open from the manipulating device at one end of each of the other ducts.

Some other modifications can be provided as follows. Unlike the present embodiment where the plural positioning grooves 7 extend from the drain port 5h almost radially on the bottom 5t, some other extending patterns can be adopted. The radial-pattern grooves may be dedicated to guide the various types of fluid to the drain port 5h in the bath 5 and, separately from the grooves, another groove for positioning the tray 10 to the bath 5 may be formed on the bottom 5t. Alternatively, the grooves may be consistent in their arrangement with the contour of the bottom 10t of the tray 10 providing the mounting plane, still providing advantages similar to the foregoing.

Moreover, the present embodiment adopts a wholly mutual-contacted manner between the first positioning pin 6 and the first through-hole 21 and a wholly tightly contacted manner between the second positioning pin 11 and the second through-hole 22. However, this is just an example. If the endoscope 20 is positionally stationary after the pin insertion, it is possible to adopt a partly mutual-contacted manner between each pin and each through-hole. For example, a cross section of each pin, which is perpendicular to the axis thereof, should not be limited to be circular. Each of the positioning pins 6 and 11 may be produced to have another cross section which partly touches the inner surface of each of the through-holes 21 and 22.

Second Embodiment

Referring to FIGS. 6-10, an endoscope washer disinfector according to a second embodiment of the present invention will now be described.

Compared to the endoscope washer disinfector 1 according to the first embodiment, the endoscope washer disinfector according to this second embodiment is different in that the first positioning pin and the second positioning pin are placed concentrically in the insertion direction. The other components are the same or similar as or to that of the first embodiment, so that those components are given the same reference numerals as those in the first embodiment for omitting those components. Only different components will now be described.

Figure 10:
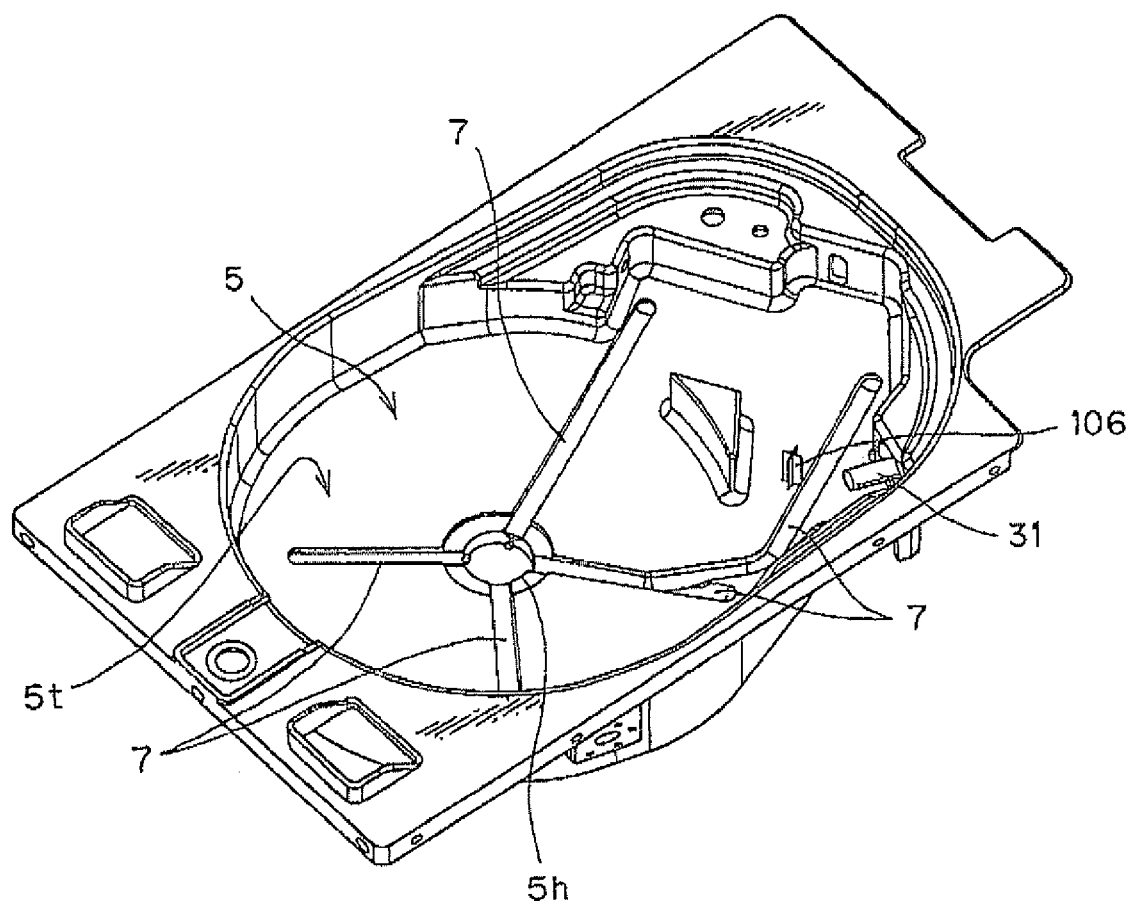
FIG. 10 is a perspective view showing only the washing disinfecting bath unit in the second embodiment.

As shown in FIG. 10, a first positioning pin 106 is placed to be close to one of the grooves 7, which is in proximity to the supply nozzle 31, so that the pin 106 stands up from the bottom 5t of the washing disinfecting bath 5. The plan view of the first positioning pin 106 is cruciform, which consists of four blade members 106BD. In FIG. 10, the first positioning pin 106 stands up at a position different from that of the first positioning pin 6 in the first embodiment, but may be designed to stand up at the same position as that in the first embodiment.

Figure 7:
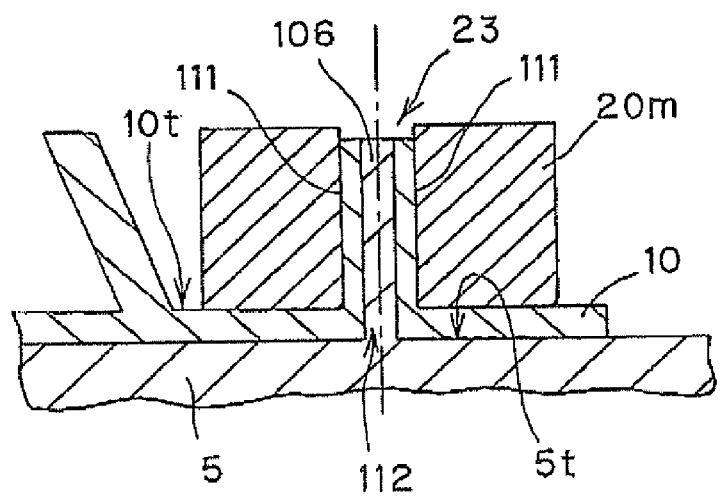
FIG. 7 is a partial sectional view taken along a VII-VII line shown in FIG. 6.

As shown in FIGS. 6 and 7, the first positioning pin 106 is in charge of not only positioning the endoscope 20 relative to the washing disinfecting bath 5 but also positioning the tray 10 relative to the bath 5, when the tray 10 with the endoscope 20 accommodated therein is loaded into the bath 5. The former positioning is achieved by having the first positioning pin 106 fit into a third though-hole 23 (later described) formed through the endoscope 20, in which the pin 106 is partly touched to the inner wall of the third through-hole 23. That is, the radial end faces of the four blade members 106BD are made to touch the third through-hole 23. Meanwhile, the latter positioning is achieved by having the first positioning pin 106 fit into a first positioning-pin insertion hole 112 (later described) formed through the tray 10, in which the pin 106 is partly touched to the inner wall of the insertion hole 112.

Practically, the first positioning pin 106 positions both the tray 10 and the endoscope 20 such that the manipulating device 20m of the endoscope 20 is located close to the supply nozzle 31 at an automatic connection position, where the mouth ring 25 thereof is directly opposed to the supply nozzle 31 and may be automatically connected with the supply nozzle 31.

Figure 9:
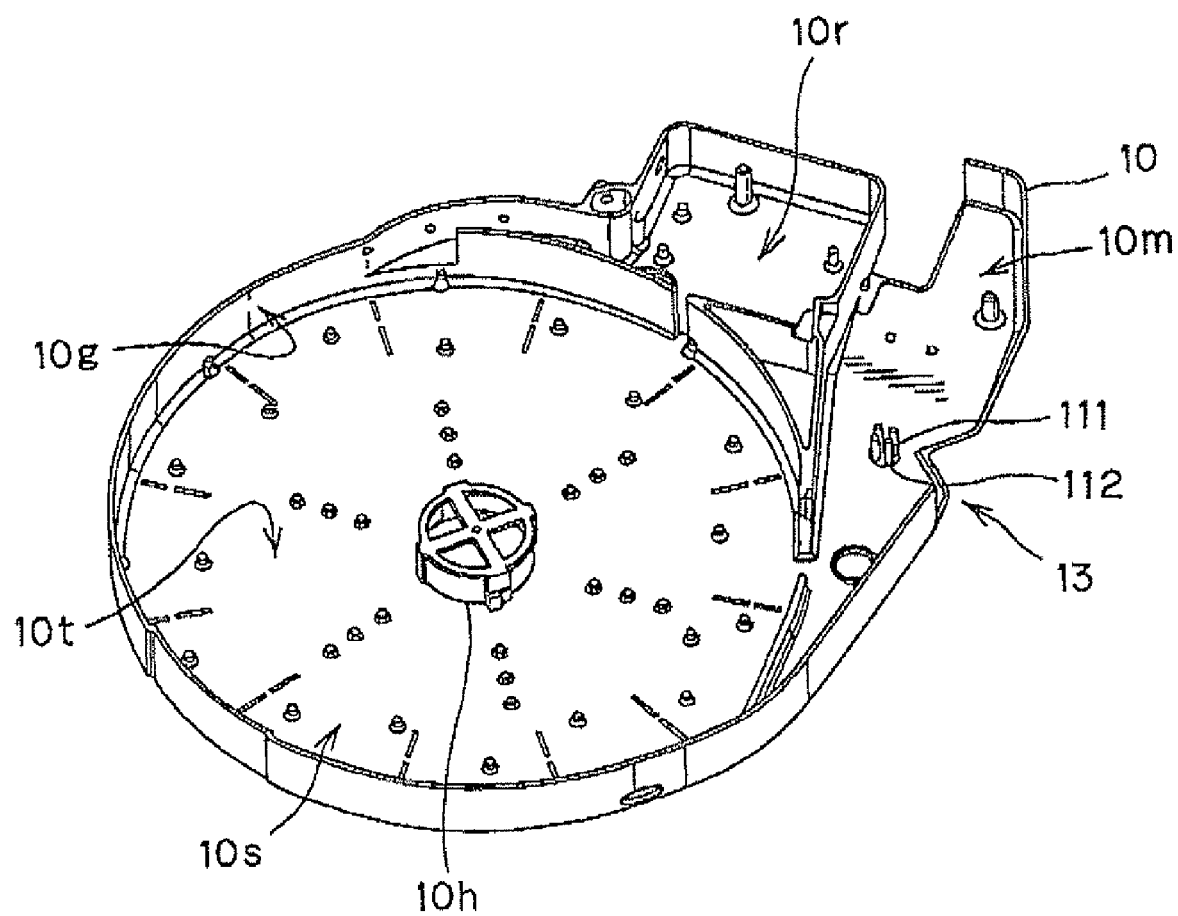
FIG. 9 is a perspective view showing the tray to be loaded into the washing disinfecting bath in the second embodiment.

FIG. 9 shows the bottom 10t of the manipulating-device accommodation space 10m of the tray 10. On the bottom 10t, the first positioning-pin insertion hole 112 is located, through which the first positioning pin 106 is formed to be inserted when the tray 10 is loaded into the washing disinfecting bath 5.

The first positioning-pin insertion hole 112 is produced to have a diameter which allows the first positioning pin 106 to partly touch the wall of this hole 112. In addition, this hole 112 is located face to face with the first positioning pin 106, when the tray 10 is loaded into the washing disinfecting bath 5.

Furthermore, on the bottom 10t of the manipulating-device accommodation space 10m, a second positioning pin 111 is fixed at a position to stand up thereat. The position of this pin 111 is decided so as to avoid, in the plane of the bottom 10t, an interference with the first positioning pin 106, in cases where the pin 106 is inserted into the first positioning-pin insertion hole 112. The second positioning pin 111 is shaped into a cross shape consisting of four blade members 111BM, but with no central part, which protrudes along four radial directions within the first positioning-pin insertion hole 112, when viewed vertically as shown in FIG. 6.

The second positioning pin 111 is located to become concentric with the first positioning pin 106 as to their central axes, whenever the tray 10 is loaded into the washing disinfecting bath 5.

When the manipulating device 20m is placed into the manipulating-device accommodation space 10m, the second positioning pin 111 is forcibly inserted into the third through-hole 23 formed through the endoscope 20, as shown in FIGS. 6 and 7. In this inserted state, part of the pin 111 (i.e., the radial end faces of the four blade members 111BM) is made to touch the wall of the third through-hole 23, providing the endoscope 20 with a positioning function to the tray 10.

To be specific, the second positioning pin 111 positions the endoscope 20 such that the mouth ring 25 thereof is opposed to the insertion opening 13. As a result, whenever the tray 10 is loaded into the washing disinfecting bath 5, the mouth ring 25 is located at the automatic connection position, where the mouth ring 25 is directly opposite to the supply nozzle 31.

Figure 8:
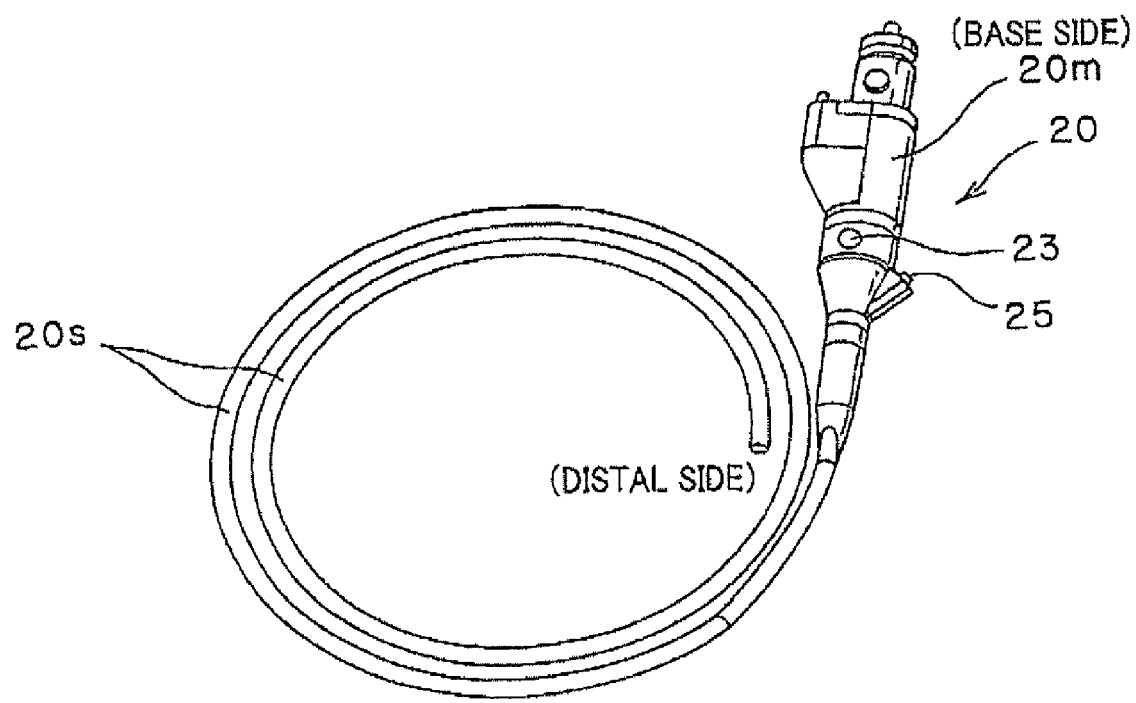
FIG. 8 is a perspective view showing the endoscope to be accommodated in the washing disinfecting bath in the second embodiment.

FIG. 8 shows the manipulating device 20m of the endoscope 20, in which the third through-hole 23 is formed through the device 20m and serves as a positioning hole which allows both the first and second positioning pins 106 and 111 to be inserted forcibly therethrough.

Incidentally, the third through-hole 23 has a diameter which allows the first and second positioning pins 106 and 111 to be partly in contact with the wall of the third through-hole 23. Further, the third through-hole 23 may be formed as a bottomed hole.

The operations and advantages of the second embodiment will now be described.

Similarly to the case in the first embodiment, for washing and disinfecting a used endoscope 20, the endoscope 20 is first accommodated in the tray 10, prior to loading the tray 10 into the washing disinfecting bath 5. Practically, as shown in FIG. 8, the insertion tube 20s is wound, earlier, as shown in FIG. 6, being accommodated into the insertion-tube accommodation space 10s. Then the manipulation device 20m is accommodated into the manipulating-device accommodation space 10m.

In accommodating the manipulating device 20m into the accommodation space 10m, the second positioning pin 111 is forcibly inserted into the third through-hole 23 of the manipulating device 20m in a party-contacted manner with the wall of this through-hole 23, as shown in FIGS. 6 and 7, Since the second positioning pin 111 stands up from the bottom 10t of the manipulating-device accommodation space 10m, the mouth ring 25 is located facing the insertion opening 13. In this state, the endoscope 20 is positioned relative to the tray 10.

The remote control is also accommodated in the remote-control accommodation space 10r of the tray 10.

Next the tray 10 with the endoscope 10 mounted therein is loaded into the washing disinfecting bath 5. That is, as described, the plural tubular convex parts PT on the bottom lot of the rear side of the tray 10 are fitted into the plural grooves 7 on the bottom 5t of the bath 5. In parallel with this, as shown in FIGS. 6 and 7, the first positioning pin 106 standing up from the bottom 5t of the bath 5 is inserted into the first positioning-pin insertion hole 112 of the tray 10 in a manner that the pin 106 does not touch the second positioning pin 111. In addition, the pin 106 is inserted into the third through-hole 23 of the manipulating device 20m in a manner that the pin 106 partly touches the third through-hole 23.

As a result, the plural grooves 7 and the first positioning pin 106 allow the mouth ring 25 to be located at the automatic connection position facing the supply nozzle 31, like the case in the first embodiment.

Accordingly, the endoscope 20 accommodated in the tray 10 can be accommodated in the bath 5 with high accuracy. The top cover 3 is then closed, the washer disinfector 1 is switched on, so that the supply nozzle 31 is moved toward the mouth ring 25 of the endoscope 20 for automatic connection therewith. Various kinds of fluids are supplied into the therapeutic-instrument insertion duct via the mouth ring 25 from the supply nozzle 31 during the washing and disinfecting processes.

In this way, using the third through-hole 23 which accepts the insertion of the first positioning pin 106 in a partly touched manner to the through-hole 23, both the tray 10 and the endoscope 20 are positioned relative to the washing disinfecting bath 5 at the same time.

Also, used are the first positioning-pin insertion hole 112 which accepts the first positioning pin 106 and the third through-hole 23 which accepts the second positioning pin 111 in a partly-touched manner with the through-hole 23, in which both pins 111 and 106 are concentrically arranged. By this, the second positioning pin 111 is able to position the endoscope 20 relative to the tray 10.

Hence, advantages similar to those in the first embodiment can be obtained. Additionally there is another advantage resulting from the structure in which both of the first and second positioning pins 106 and 111 are partly touched to the third through-hole 23. Thanks to such structures, various kinds of fluids for washing and disinfection can be circulated through the gaps formed between the positioning pins 106 and 111 and the through-hole 23. Although such gaps are subjected to accumulation of dirt, circulating the fluid will surely increase the washing and disinfecting performance for the endoscope 20.

The foregoing operations are true of the ducts of the endoscope 20 other than therapeutic-instrument insertion duct, providing similar advantages to the above.

In the present embodiment, some other modifications can be provided as follows. Unlike the present embodiment where the plural positioning grooves 7 extend from the drain port 5h almost radially on the bottom 5t, some other extending patterns can be adopted. The radial-pattern grooves may be dedicated to guide the various types of fluid to the drain port 5h in the bath 5 and, separately from the grooves, another groove for positioning the tray 10 to the bath 5 may be formed on the bottom 5t. Alternatively, the grooves may be consistent in their arrangement pattern with the contour of the bottom 10t of the tray 10 providing the mounting plane, still providing advantages similar to the foregoing.

Other Embodiments

By the way, some cases may arise where, when the tray 10 with the endoscope 20 mounted therein is loaded into the bath 5, the mouth ring 25 of the manipulating device 20mn may slightly shift from the automatic connection position even if the structures according to the first or second embodiment are employed. In the following, the structure will now be described which allows the supply nozzle 31 to be connected with the mouth ring 25 more reliably, even when such a positional shift happens.

Figure 11:
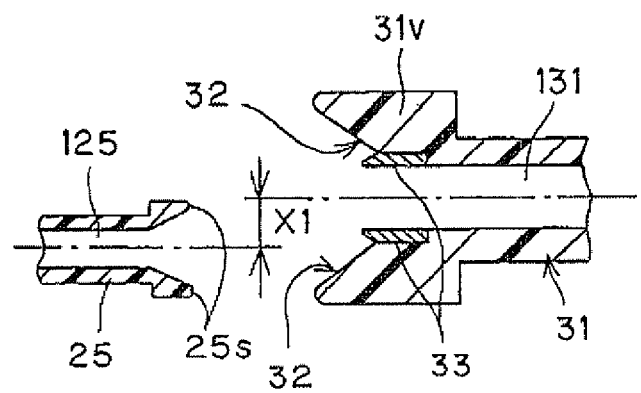
FIG. 11 is a partial sectional view that explains the connection between the mouth ring and the supply nozzle in another embodiment of the present invention.

FIG. 11 shows a connection end 31v attached to the supply nozzle 31. This connection end 31v covers the outer circumferential surface of the mouth ring 25 of the endoscope 20. The connection end 31v has a tapered inner circumferential surface 32 formed such that the diameter of the opening gradually becomes smaller as the distance advances inside along the axial direction from the end thereof.

Figure 13:
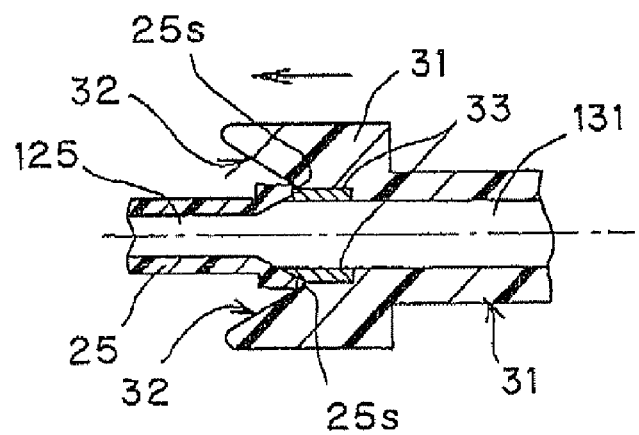

Thus, when being connected to the mouth ring 25 automatically by a known automatic electrical mechanical mechanism (not shown), a ring-shaped tip 25s of the mouth ring 25 is made to touch the inner circumferential surface 32 of the connection end 31v, as shown in FIG. 13. The connection end 31v is equipped with a ring-shaped elastic member 33 made of, for example, rubber. This member 33 is positionally consistent with the ring-shaped tip 25s, when being connected completely. The connection end 31v is made of self-lubricating material such as plastic resin including polyacetal resin.

Figure 12:
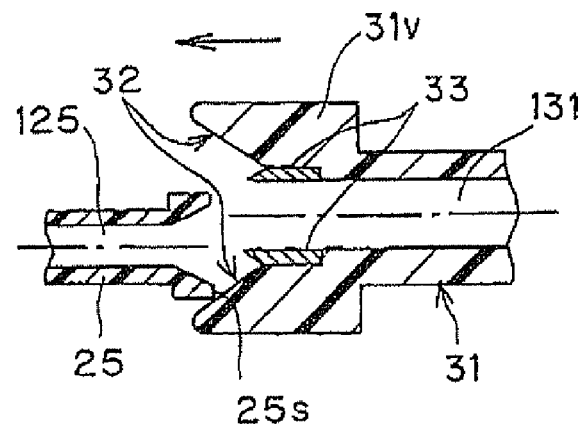
FIGS. 12 and 13 are other partial sectional views that explain the connection of the mouth ring and the supply nozzle shown in FIG. 11.

Hence, even if the mouth ring 25 is positionally deviated from the supply nozzle 31 by an amount X1 as illustrated in FIG. 11, the mutual relative positions of both the mouth ring 25 and the connection end 31v are corrected during the travel of the supply nozzle 31. The reason is that, as shown in FIG. 12, the ring-shaped tip 25s which has contacted the tapered inner circumferential surface 32 of the connected end 31v is contacting a self-lubricating surface. Hence both the supply nozzle 31 and the mouth ring 25 are mutually guided to make their fluid supply paths 131 and 125 the same level, as shown in FIG. 13. That is, both central axes of the fluid supply paths 131 and 125 are aligned.

When the connection is completed, the ring-shaped tip 25s of the mouth ring 25 forcibly presses the elastic member 33, the connection end 31v is connected with the mouth ring 25 to cover the ring-shaped tip 25s as shown in FIG. 13, providing a watertight communication between both fluid supply paths 131 and 125.

Hence, even if the tray 10 is loaded into the base 5 and causes a situation where the mouth ring 25 is positionally shifted from the supply nozzle 31, i.e., the automatic connection position, the tapered inner circumferential surface 32 corrects the mutual positions within a design allowance. It is therefore possible to load the supply nozzle 31 to the mouth ring 25 more reliably.

Of course, the above structure of the supply nozzle 31 can be applied to mouth rings other than the mouth ring 25 of the therapeutic-instrument insertion duct, still providing the same position-correcting advantage.

Figure 14:
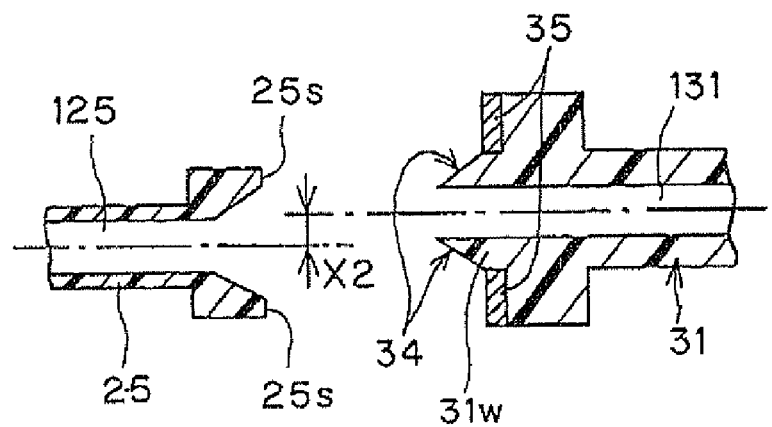
FIGS. 14 and 15 are partial sectional views that explain the connection between the mouth ring and the supply nozzle in another embodiment of the present invention.
Figure 15:
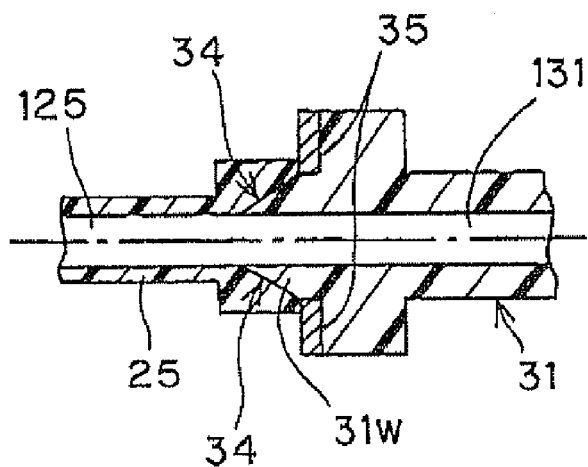

Referring to FIGS. 14 and 15, a modification showing another connection method between the supply nozzle and the mouth ring will now be described.

FIG. 14 shows a supply nozzle 31 with a connection end 31w to be fitted into the mouth ring 25 of the endoscope 20 during the automatic connecting procedure. The connection end 31w has a tapered outer circumferential surface 34 the diameter of which becomes larger as the distance advances inside along the axial direction from the end thereof.

The connection end 31w has a part on its outer circumferential surface 34, which touches the ring-shaped tip 25s of the mouth ring 25 when the connection is completed. An elastic member 35, such as rubber, is arranged on that part of the surface 34. The connection end 31w is made of self-lubricating material such as such as plastic resin including polyacetal resin.

Thus, as shown in FIG. 14, when a positional difference X2 between the mouth ring 25 and the supply nozzle 31 is caused during movement of the supply nozzle 31, the outer circumferential surface 34 is able to provide a positional correction function because of a combination of its tapered surface and its self-lubricating property. The mutual relative positions between both fluid supply paths 131 and 125 of the supply nozzle 31 and the mouth ring 25 are corrected automatically during the travel of the supply nozzle 31, as shown in FIG. 15.

When the connection is completed, the ring-shaped tip 25s of the mouth 25 forcibly presses the elastic member 35, providing a watertight communication between the fluid supply paths 131 and 125.

Hence the supply nozzle 31 shown in FIG. 14 has the capability of automatically correcting the mutual relative positional difference within a given allowable margin, so that the supply nozzle 31 can be watertight-connected to the mouth ring 25 more reliably.

The above structure of the supply nozzle 31 can also be applied to mouth rings other than the mouth ring 25 of the therapeutic-instrument insertion duct, still providing the same position-correcting advantage.

Figure 16:
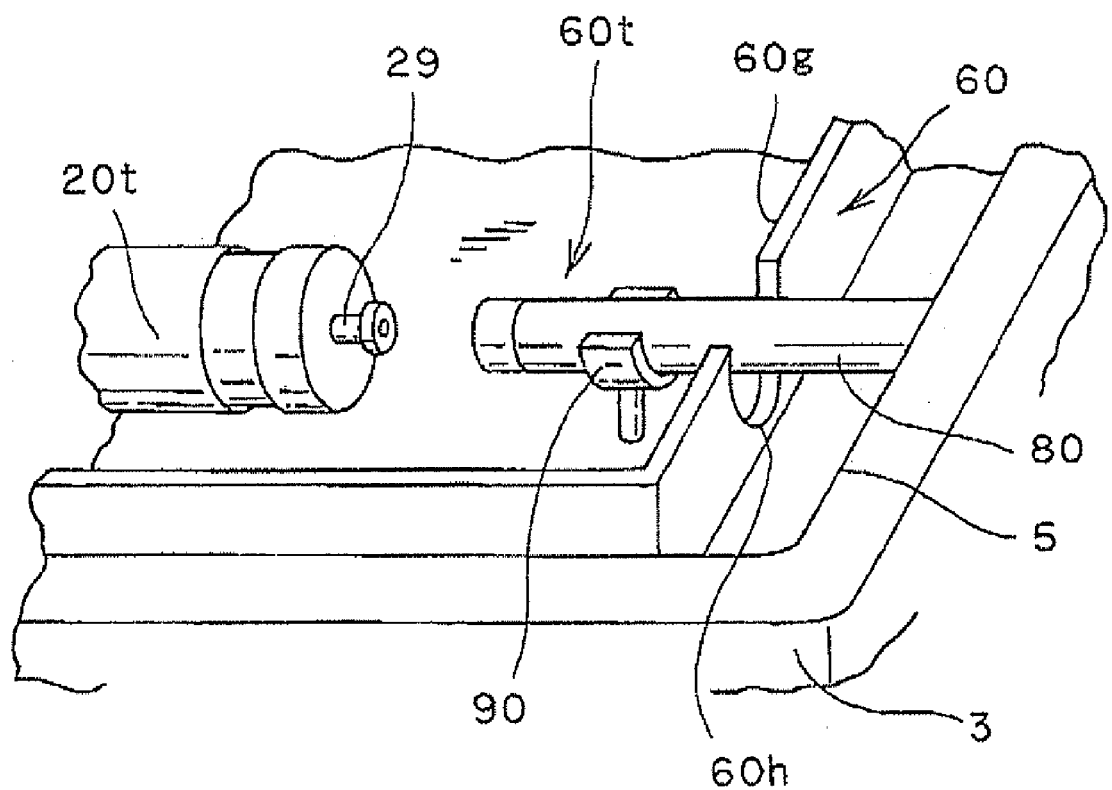
FIG. 16 is a partial perspective view showing how a supply nozzle is connected to the mouth ring in another embodiment of the present invention.

Referring to FIG. 16, a further embodiment will now be described. This embodiment also concerns a modification of the supply nozzle, which is able to prevent the supply nozzle from shifting from the automatic connection position.

FIG. 16 shows a nozzle support member 90 that supports a supply nozzle 80 on a tray 60. This example shows an example in which the supply nozzle 80 is detachably connected with a mouth ring 29 extended from the end of, for example, an air-supply water-supply duct of the endoscope 20. That is, the mouth ring 29 is located on the base end 20t of the manipulating device 20m of the endoscope 20.

There is a fluid supply unit (not shown) equipped with the elongated supply nozzle 80 oriented to the washing disinfecting bath 5, as shown in FIG. 16.

The tray 60 has a side wall 60g, which faces the supply nozzle 80 when the tray 60 is loaded into the bath 5. The side wall 60g has an insertion opening 60h though which the supply nozzle 80 passes. Between the insertion opening 60h and the mouth ring 29 of the air-supply water-supply duct, a nozzle support member 90 fixedly stands up from the bottom 60t of the tray 60. The nozzle support member 90, which has a surface that is curved according to the curvature of the outer circumferential surface of the supply nozzle 80, is in charge of supporting the supply nozzle 80 so that the nozzle 80 keeps its position facing the mouth ring 29 without any positional shift. The nozzle support member 90 may be placed on the bottom 5t of the bath 5.

Components other then the bath 5 and tray 60 are the same as those in described already.

In this way, the nozzle support member 90 is arranged to support the given circumferential angular range of the supply nozzle 80, with the result that the supply nozzle 80 is prevented from shifting from the automatic connection position. Hence it is possible to provide a stable and reliable connection of the supply nozzle 80 to the mouth ring 29, even if the supply nozzle 80 has an elongated outer shape.

The above nozzle support member 90 may also be applied to other mouth rings for the therapeutic-instrument insertion duct and others and is able to provide equivalent advantages to the above.

MODIFICATIONS

According to the present invention, various modifications can also be provided.

A first modification exemplifies how to decide the orientation of the tray 10 relative to the washing disinfecting bath 5. In the foregoing embodiments, the plural tubular convex parts PT are formed on the rear side of the bottom 10t (serving as an endoscope mounting plane) of the tray 10, while the plural linear grooves 7 into which the tubular convex parts PT are fit are formed on the bottom 5t of the base 5. In contrast, this concave-convex relationship may be formed in the opposite manner. In other words, the liner grooves may be formed on the rear side of the bottom of the tray 10, and the tubular convex parts may be formed on the bottom 5t of the bath 5.

A second modification concerns the positioning through-hole (21, 22; 23) which is formed at the manipulating device 20m and which serves as a latching part to position the manipulating device 20m to the tray 10 and the washing disinfecting bath 5.

Figure 17:
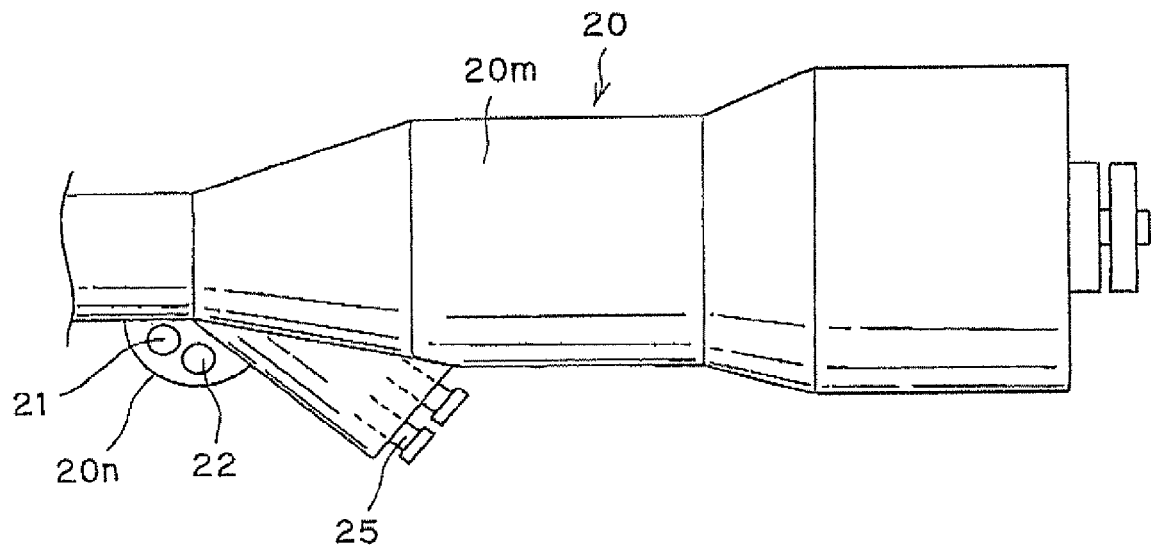
FIG. 17 is a partial side view showing where positioning through-holes are formed in a modification.

It is not always necessary to produce this positioning through-hole at the main body itself of the manipulating device 20. For example, as shown in FIG. 17, a protruding portion 20n is integrally added to, for examples a distal-side part of the manipulating device 20m and such a positioning through-hole is formed through the added protruding portion 20n. The example shown in FIG. 17 provides the positioning through-holes 21 and 22 as a modification of the structure shown in the first embodiment. By producing such positioning through-holes at peripheral positions deviating from the central part of the manipulating device 20m, the present invention can be put into practice without changing or re-designing the internal structure itself of this device 20m.

A third modification concerns another way of making the first and second positioning pins 106 and 111 touch the circumferential wall surface of the poisoning through-hole 23, that is, a modification from the second embodiment.

Figure 18:
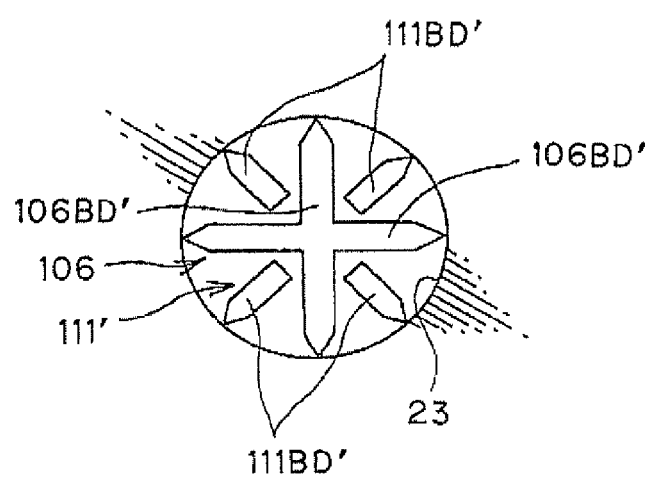
FIG. 18 is a sectional view showing how positioning pins touch the wall of a positioning through-hole.

In the second embodiment, each of the positioning pins 106 and 111 is formed to have radially-extended arm portions each having a specified, but limited, area on the radially-directed tip face thereof. The specified area enables each of the pins 106 and 111 to touch the through-hole 23 with planar contact. In contrast, as shown in FIG. 18, the modification exemplifies a first positioning pin 106' and a second positioning pin 111' which are able to touch the through-hole 23 with line contact or point contact. This is because each of the positioning pins 106' and 111' is formed to have radially-extended arm portions each having a pointed radially-directed tip. The pointed tips enable each of the pins 106' and 111' to touch the through-hole 23 with line or point contact. Thus hardly any substance or dirt can remain between the wall surface of the positioning through-hole 23 and the positioning pins 106' and 111', enhancing the washing and disinfection effect.

Although the description above contains many specificities, these should not be construed as limiting the scope of the invention but as merely providing illustrations of some of the presently preferred embodiments of the present invention. Thus the scope of the present invention should be determined by the appended claims.

What is claimed is:

1. An endoscope washer disinfector for washing and disinfecting an endoscope equipped with a mouth ring and an insertion tube through which a duct is formed, the mouth ring communicating with the duct, the endoscope washer disinfector comprising:

a washing disinfecting bath in which the endoscope is accommodated;
   a nozzle arranged with the washing disinfecting bath, loaded into the mouth ring of the endoscope, and is in charge of supplying fluid to the duct via the mouth ring;
   a tray on which the endoscope is mounted and which is detachably loaded into the washing disinfecting bath;
   a direction deciding member that decides a loading direction of the tray such that the tray loaded into the washing disinfecting bath is positioned in a given direction on which the mouth ring is positioned relative to the nozzle, the direction deciding member including a groove formed on the washing disinfecting bath and a convex part formed on the tray to be fit into the groove;

a bilateral positioning member that positions the endoscope and the tray such that the mouth ring of the endoscope mounted on the tray is located at a given position in the tray; and a trilateral positioning member that positions the washing disinfecting bath, the tray, and the endoscope such that, when the tray is loaded into the washing disinfecting bath, the mouth ring of the endoscope positioned at the given position in the tray by the bilateral positioning member is positioned at a position that is across from the nozzle in the washing disinfecting bath, wherein the groove consists of a plurality of grooves radially extending from a central part of a bottom of the washing disinfecting bath, and the convex part includes a plurality of tubular convex parts which are allowed to be fit into the plurality of grooves when the tray is loaded into the washing disinfecting bath.

2. An endoscope washer disinfector for washing and disinfecting an endoscope equipped with a mouth ring and an insertion tube through which a duct is formed, the mouth communicating with the duct, the endoscope washer disinfector comprising:

a washing disinfecting bath in which the endoscope is accommodated;

a nozzle arranged with the washing disinfecting bath, loaded into the mouth ring of the endoscope, and is in charge of supplying fluid to the duct via the mouth ring;

a tray on which the endoscope is mounted and which is detachably loaded into the washing disinfecting bath;

a bilateral positioning member that positions the endoscope and the tray such that the mouth ring of the endoscope mounted on the tray is located at a given position in the tray; and a trilateral positioning member that positions the washing disinfecting bath, the tray, and the endoscope such that, when the tray is loaded into the washing disinfecting bath, the mouth ring of the endoscope positioned at the given position in the tray by the bilateral positioning member is positioned at a position that is across from the nozzle in the washing disinfecting bath, wherein the bilateral positioning member includes a first pin member standing up from the tray, the first pin member being allowed to pass through a positioning through-hole formed through a manipulating device so that the first pin member is latched with the positioning through-hole of the manipulating device when the endoscope is mounted on the tray, the first pin member having an insertion through-hole formed at the standing-up position of the first pin member, and the trilateral positioning member includes a second pin member standing up from the washing disinfecting bath, the second pin member being allowed to pass through the insertion through-hole of the first pin member so that the second pin member is latched with the positioning through-hole when the tray is loaded into the washing disinfecting bath.

3. The endoscope washer disinfector of claim 2, wherein each of the first and second pin members have a plurality of blade parts radially extending in a section perpendicular to a direction along which the first and second pin members stand up, and the plural blade parts of the first pin member and the plural blade parts of the second pin member extend so as to avoid a positional interference from one the other and touches the positioning through-hole.

4. The endoscope washer disinfector of claim 3, wherein the plural blade parts of each of the first and second pin members touch the positioning through-hole with point or plane contact.

* * * * *